United States Patent [19]

Carozzi et al.

[11] Patent Number: 5,204,100

[45] Date of Patent: Apr. 20, 1993

[54] *BACIULLUS THURINGIENSIS* STRAINS ACTIVE AGAINST COLEOPTERAN INSECTS

[75] Inventors: Nadine B. Carozzi, Raleigh; Vance C. Kramer, Hillsborough; Gregory W. Warren; Michael G. Koziel, both of Cary, all of N.C.

[73] Assignee: Ciba-Geigy Corporation, Ardsley, N.Y.

[21] Appl. No.: 703,421

[22] Filed: May 21, 1991

Related U.S. Application Data

[63] Continuation-in-part of Ser. No. 650,792, Feb. 1, 1991, abandoned.

[51] Int. Cl.$^5$ .................. A01N 63/00; C12N 1/20
[52] U.S. Cl. .................. 424/93 L; 435/252.5; 435/832
[58] Field of Search ............... 435/252.5, 252.31, 832; 424/93 L

[56] References Cited

U.S. PATENT DOCUMENTS

| | | | |
|---|---|---|---|
| 4,851,340 | 7/1989 | Krieg et al. | 435/68 |
| 4,889,918 | 12/1989 | Krieg et al. | |
| 4,910,016 | 3/1990 | Gaertner et al. | 424/93 |
| 4,973,676 | 11/1990 | Krieg et al. | |
| 4,999,192 | 3/1991 | Payne et al. | 424/93 |
| 5,002,765 | 3/1991 | Herrnstadt et al. | 424/93 |
| 5,024,837 | 6/1991 | Donovan et al. | 424/93 |

FOREIGN PATENT DOCUMENTS 0382990 8/1990 European Pat. Off. .

OTHER PUBLICATIONS

Aronson et al., *Microbiol. Rev.*, 50:1-24 (1986).
Wilcox et al., in Protein Engineering, Academic Press, Inc., New York (1986) pp. 395-413.
Whiteley and Schnepf, Ann. Rev. Microbiol., 40:549-576 (1986).
Hofte and Whiteley, *Microbiological Reviews*, 53:242-255 (1989).
Hofte et al., *Applied and Environmental Microbiol.*, 54:2010-2017 (1988).
Martin et al., *BioTechniques*, 3:386-392 (1985).
Kronstad and Whiteley, Gene, 43:29-40 (1986).

*Primary Examiner*—Robert A. Wax
*Assistant Examiner*—Keith D. Hendricks
*Attorney, Agent, or Firm*—Steven L. Lazar; W. Murray Spruill

[57] ABSTRACT

Four new strains of *Bacillus thuringiensis* are disclosed which are active against Coleoptera. The novel strains are identified through PCR technology using mixtures of carefully selected oligonucleotide primers that aid in the prediction of insect toxicity profile for the proteins produced by the strains.

6 Claims, No Drawings

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear (i i) MOLECULE TYPE: DNA (genomic)

(i i i) HYPOTHETICAL: NO (i v) ANTI-SENSE: NO (v i) ORIGINAL SOURCE:
                (A) ORGANISM: OLIGONUCLEOTIDE PRIMER Lep1A (x i) SEQUENCE DESCRIPTION: SEQ ID NO:1:

CCGGTGCTGG ATTTGTGTTA                                                                    20

(2) INFORMATION FOR SEQ ID NO:2:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
                (A) ORGANISM: Oligonucleotide Primer Lep1B (x i) SEQUENCE DESCRIPTION: SEQ ID NO:2:

AATCCCGTAT TGTACCAGCG                                                                    20

(2) INFORMATION FOR SEQ ID NO:3:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
                (A) ORGANISM: Oligonucleotide primer Lep2A (x i) SEQUENCE DESCRIPTION: SEQ ID NO:3:

CCGAGAAAGT CAAACATGCG                                                                    20

(2) INFORMATION FOR SEQ ID NO:4:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
                (A) ORGANISM: Oligonucleotide primer Lep2B (x i) SEQUENCE DESCRIPTION: SEQ ID NO:4:

TACATGCCCT TTCACGTTCC                                                                    20

(2) INFORMATION FOR SEQ ID NO:5:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Oligonucleotide primer Dip1A ( x i ) SEQUENCE DESCRIPTION: SEQ ID NO:5:

CAAGCCGCAA ATCTTGTGGA 20

( 2 ) INFORMATION FOR SEQ ID NO:6:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Oligonucleotide Primer Dip1B ( x i ) SEQUENCE DESCRIPTION: SEQ ID NO:6:

ATGGCTTGTT TCGCTACATC 20

( 2 ) INFORMATION FOR SEQ ID NO:7:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Oligonucleotide Primer Dip2A ( x i ) SEQUENCE DESCRIPTION: SEQ ID NO:7:

GGTGCTTCCT ATTCTTTGGC 20

( 2 ) INFORMATION FOR SEQ ID NO:8:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Oligonucleotide Primer Dip2B ( x i ) SEQUENCE DESCRIPTION: SEQ ID NO:8:

TGACCAGGTC CCTTGATTAC                                                                                        20

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Oligonucleotide Primer Col1A ( x i ) SEQUENCE DESCRIPTION: SEQ ID NO:9:

GTCCGCTGTA TATTCAGGTG                                                                                        20

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Oligonucleotide Primer Col1B ( x i ) SEQUENCE DESCRIPTION: SEQ ID NO:10:

CACTTAATCC TGTGACGCCT                                                                                        20

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Oligonucleotide Primer Col2A ( x i ) SEQUENCE DESCRIPTION: SEQ ID NO:11:

AGGTGCCAAC TAACCATGTT                                                                                        20

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO

-continued ( i v ) ANTI-SENSE: NO ( v i ) ORIGINAL SOURCE:
        ( A ) ORGANISM: Oligonucleotide Primer Col2B ( x i ) SEQUENCE DESCRIPTION: SEQ ID NO:12:

GATCCTATGC TTGGTCTAGT                                              20

( 2 ) INFORMATION FOR SEQ ID NO:13:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: OLIGONUCLEOTIDE PRIMER NC107

( x i ) SEQUENCE DESCRIPTION: SEQ ID NO:13:

CTGAGAGGGA ACAACCTG                                               18

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: OLIGONUCLEOTIDE PRIMER NC108

( x i ) SEQUENCE DESCRIPTION: SEQ ID NO:14:

CTCAATGTTG TTCTGAGTGA                                            20

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bt Positive Control PI- PLC Primer A ( x i ) SEQUENCE DESCRIPTION: SEQ ID NO:15:

CGCTATCAAA TGGACCATGG                                            20

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
(A) ORGANISM: Bt Positive Control PI- PLC Primer B (x i) SEQUENCE DESCRIPTION: SEQ ID NO:16:

GGACTATTCC ATGCTGTACC 20

BACIULLUS THURINGIENSIS STRAINS ACTIVE AGAINST COLEOPTERAN INSECTS

The present invention is a continuation-in-part of patent application Ser. No. 07/650,792, filed on Feb. 1, 1991.

BACKGROUND OF THE INVENTION

The present invention relates to novel strains of bacteria, particularly bacteria of the species *Bacillus thuringiensis*, which demonstrate insecticidal activity against members of the order Coleoptera. These bacterial strains may be useful in insecticidal compositions, as well as for development of further methods of control of insects.

*Bacillus thuringiensis* (Bt) is a gram-positive soil bacterium characterized by its ability to produce parasporal crystal protein inclusions (delta endotoxins) during sporulation. These crystal inclusions contain proteins, many of which display a highly specific insecticidal activity. Most strains are active against caterpillar larvae of the order Lepidoptera. Several strains show activity against larvae of certain members of the order Diptera, and several strains have activity against some larvae of the order Coleoptera. Various Bt insecticidal proteins are reviewed in numerous prior art sources, including for example, Aronson et al., Microbiol. Rev. 50:1-24 (1986); Wilcox et al., Protein Engineering, Academic Press, New York, N.Y., pp.395-413, (1986); Whiteley and Schnepf, Ann. Rev. Microbiol. 40:549-76 (1986), and Hofte and Whiteley, Microbiol. Rev. 53:242-255 (1989).

Only a few strains of *Bacillus thuringiensis* have been identified that are active against insects of the order Coleoptera. U.S. Pat. No. 4,851,340 (Krieg et al.) relates to a strain *Bacillus thuringiensis* var. tenebrionis (deposited at DSM 2803) which is disclosed to be toxic to Coleoptera, while being substantially non-toxic to Lepidoptera and Diptera. U.S. Pat. No. 4,889,918 (Krieg et al.) relates to a toxin from about 65 to about 70 kilodaltons in weight, produced by the strain *Bacillus thuringiensis* var. tenebrionis (deposited at DSM 2803). U.S. Pat. No. 4,973,676 (Krieg et al.) relates to a DNA sequence encoding the toxin produced by the strain *Bacillus thuringiensis* var. tenebrionis (deposited at DSM 2803). U.S. Pat. No. 4,910,016 (Gaertner et al.) relates to a *Bacillus thuringiensis* strain MT 104, which is disclosed to be active against insect pests of the orders Coleoptera and Lepidoptera. European Patent Application Publication No. 0 382 990 relates to two *Bacillus thuringiensis* strains, PGS1245 and PGS1208.

The prior art has disclosed various methods of identifying Bt strains producing insecticidal proteins. These methods include: 1) use of monoclonal antibodies, 2) insect bioassays, 3) biochemical assays, and 4) hybridization assays.

Monoclonal antibodies to insecticidal proteins of *Bacillus thuringiensis* have been made [Hofte et al., Applied Envir. Microbiol. 54:2010-2017 (1988)] and used to characterize various classes of insecticidal Bt proteins [Peferoen, Symposium on the Analytical Chemistry of *Bacillus thuringiensis*, American Chemical Society]. This technique has the disadvantage of requiring the lengthy identification, characterization and production of monoclonal antibodies. Monoclonal antibodies provide limited information about the genes producing the proteins that are recognized by a given antibody.

Insect bioassays have been used to characterize large numbers of *Bacillus thuringiensis* isolates. This technique has the disadvantage of being time consuming and labor intensive. In addition to limiting the number of strains characterized, this method does not readily discriminate among different genes and makes redundant testing of the same strains likely.

Biochemical assays have also been used to screen strains within the species *Bacillus thuringiensis*, [Martin techniques 3:386-392 (1985). These techniques have the disadvantage of not characterizing the genes encoding the insecticidal proteins of isolates and, therefore, not predicting insecticidal activities.

Hybridization assays have been used to characterize strains according to which of three major classes of Bt insecticidal genes they contain, [Kronstad and Whiteley, Gene 43:29-40 (1986)]. Hybridization techniques have the disadvantage of being labor intensive, time consuming, and are unable to discriminate different genes within the major insecticidal classes.

The polymerase chain reaction has been used to amplify genetic material and the details of the PCR technique are well known in the art. See, for example, Innis et al., *PCR Protocols: A Guide to Methods and Applications*, Academic Press, Inc., New York, 1990; and Erlich, *PCR Technology Principles and Applications for DNA Amplification*, Erlich, *PCR Technology Principles and Applications for DNA Amplification*, Stockton Press, New York, (1989), both of which are hereby incorporated by reference for their relevant teachings.

Wallace and Skolnick (WO 89/10414, published Nov. 2, 1989) discloses a method of using amplified sequence polymorphisms to detect variation in the genes amplified. Only human genes are exemplified and no correlation is made between the type of genetic variation and the effect on phenotypic trait.

SUMMARY OF THE INVENTION

The present invention relates to novel strains of *Bacillus thuringiensis* strains which are active against insects of the order Coleoptera, particularly the Colorado Potato Beetle. The strains of the present invention were identified utilizing PCR techniques.

The strains of the present invention are demonstrated to produce novel insecticidal proteins with significant activity against Coleoptera.

The method used to identify the Coleopteran active *Bacillus thuringiensis* strains of the present invention comprises the steps of:

(a) preparing cell material from a microorganism from a culture sample;

(b) then mixing the prepared cell material from step (a) with a mixture of oligonucleotide primers to produce a second mixture, said primers corresponding to homologous regions of genes coding for insecticidal proteins;

(c) then adding to the second mixture a DNA polymerase for sufficient time to allow amplification of DNA sequences between the oligonucleotide primers of step (b) in detectable amounts;

(d) detecting the presence or absence of the amplified DNA sequences of step (c).

Another aspect of the invention is the novel insecticidal genes contained in such microorganism strains and the proteins encoded by such unidentified insecticidal genes.

Another aspect of the invention is the proteins produced by the coleopteran active strains of the present invention. These proteins demonstrate significant toxic activity against insect pests of the order Coleoptera.

DETAILED DESCRIPTION OF THE INVENTION

To better understand the meaning and scope of the present invention, the following terms have the meaning as
i indicated when used in this specification and claims unless otherwise indicated. The references cited in the specification are hereby incorporated by reference for their relevant teachings.

Insecticidal gene: A gene obtained from or occurring in a species of microorganism that codes for a protein having insecticidal activity. It is the protein coded for by the insecticidal gene that is insecticidal; the gene is not itself insecticidal.

Bt-like gene: A gene obtained from or derived from DNA occuring in a species of the genus Bacillus that codes for a protein having insecticidal activity.

Unidentified insecticidal gene: An insecticidal gene that either 1) generates no PCR products using the oligonucleotide primers of the present invention or 2) produces a PCR product using the oligonucleotide primers of the present invention wherein such a PCR product is distinguishable from the PCR product produced by the DNA sequence from which the oligonucleotide primers are obtained. Preferably, the PCR product is distinguishable to the extent of not being substantially homologous.

Coleopteran toxic activity: The ability to kill or inhibit the deleterious effects on plants of any member of the Order Coleoptera when the toxic agent is administered to such an insect orally, exoskeletonally, subcutaneously, intramuscularly, via any injection or via any other dosage form. Examples of Coleoptera include the beetles, preferably *Leptinotarsa decimlineata* and *Diabrotica ssp.*

Dipteran toxic activity: The ability to kill or inhibit the deleterious effects of any member of the Order Diptera when the toxic agent is administered to such an insect orally, exoskeletonally, subcutaneously, intramuscularly, via any injection or via any other dosage form. Examples of Diptera include the mosquitos, preferably *Culex pipiens*.

Homologous regions: Substantial functional and/or structural equivalence between sequences of nucleotides or amino acids. Functional and/or structural differences between sequences having substantial sequence homology will be de minimus. The sequences that differ from the natural sequences are usually variants of the natural sequence. A variant of a natural sequence is a modified form of the natural sequence that performs the same function. The variant may be a mutation, or may be a synthetic sequence. A de minimus functional difference results from a nucleotide or amino acid sequence that codes for a protein having essentially the same characteristics as the native protein. Such characteristics can include, for example, immunological reactivity, enzyme activity, insecticidal activity, structural protein integrity, etc. Structural differences are considered de minimus if there is a significant amount of sequence overlap or similarity between two or more different sequences or if the different sequences exhibit similar physical properties. In the case of a nucleotide sequence, the different sequences will preferably have at least 60 percent, more preferably 70 percent, most preferably 90 percent or more sequence similarity between them. In the case of amino acid sequences, the different sequences have at least 70 percent, more preferably 80 percent, and most preferably 90 percent or more similarity between the polypeptides coded for by the amino acid sequences. Physical properties that may be similar include, for example, electrophoretic mobility, chromotography similarities, sediment gradient coefficients, spectrophotometric properties, etc.

Insecticidal activity: The ability to kill or inhibit the deleterious effects on plants of any member of the phylum arthropoda, including insects, spiders and mites.

Lepidopteran toxic activity: The ability to kill or inhibit the deleterious effects of any member of the Order Lepidoptera when the toxic agent is administered to such an insect orally, exoskeletonally, subcutaneously, intramuscularly, via any injection or via any other dosage form. Examples of Lepidoptera include the larvae of moths, preferably *Ostrinia nubilalis, Manduca sexta, Heliothis zea* and *Heliothis virescens.*

Nematodicidal toxic activity: The ability to kill or inhibit the deleterious effects on plants of any member of the Order Nematoda when the toxic agent is administered to such a nematode orally, exoskeletonally, subcutaneously, intramuscularly, via any injection or via any other dosage form. Examples of nematodes include those of the genera *Pratylenchus, Hoplolaimus, Xiphinema* and *Longidorus.*

Significantly higher mortality: A particular strain of Bacillus is said to have significantly higher mortality relative to a known strain of *Bacillus thuringiensis* if the particular strain demonstrates insecticidal effects which one skilled in the art would consider to be statistically or probabilistically significant, i.e., indicative of a true quantifiable difference in insecticidal activity rather than a merely experimental difference explainable by standard deviations of data points, when assayed against a particular insect pest.

In one embodiment of the present invention, isolated strains of *Bacillus thuringiensis* are provided which strains are active against insects of the order Coleoptera.

In another embodiment, the present invention relates to methods of controlling insect pests comprising applying an insect-controlling effective amount of an active bacterial strain to an insect pest. Applications can be in formulations having spores or crystals from a *Bacillus thuringiensis* strain together with the addition of surfactants, dispersants, inert carriers and other components, and can take the form of wettable powders, liquid concentrates, granules or other formulations. These formulation and application procedures are well known in the art.

It is one aspect of the present invention that insecticidal genes are identified in a sample of cell material using polymerase chain reaction (PCR) techniques to amplify the genetic material between known oligonucleotide primers and then detecting the PCR products. Therefore, the present invention relates to a method for identifying novel strains of *Bacillus thuringiensis* comprising the steps of:

(a) preparing cell material from a microorganism from a culture sample;

(b) then mixing the prepared cell material from step (a) with a mixture of oligonucleotide primers to produce a second mixture, said oligonucleotide primers corresponding to homologous regions of genes coding for insecticidal proteins;

(c) then adding to the second mixture a DNA polymerase for sufficient time to allow amplification of DNA sequences between the oligonucleotide primers of step (b) in detectable amounts;

(d) detecting the presence or absence of the amplified DNA sequences of step (c).

The first step in accomplishing this is to prepare cell material of microorganism strains from a sample containing one or more microbial strain. Preferred microorganisms are those of the genus Bacillus. Isolation of cell material can be accomplished by any of the isolation methods known in the art, including DNA isolation, physical disruption, lysing of the cells by lysozyme or boiling. Preferably, the cells from a culture of Bacillus are boiled at a temperature of the boiling point of the solution to about 100° C., more preferably at about 100° C. for a period of about 5 minutes to about 15 minutes, more preferably about 10 minutes. See generally, Sandhu et al., BioTechniques 7:689-690 (1989).

The prepared cell material can be exposed to the oligonucleotide primers of the PCR reaction after cooling. The methods for performing PCR amplification are well known to those of skill in the art [Wang et al., Proc. Nat. Acad. Sci. USA 86:9717-9721 (1989); Innis et al., *PCR Protocols: A Guide to Methods and Applications*, Academic Press, Inc., New York, 1990; and Erlich, *PCR Technology Principles and Applications for DNA Amplification*, Stockton Press, New York, (1989)] and can be performed on instrumentation that is commercially available from Perkin-Elmer Cetus (Norwalk, Conn.) or other suppliers].

The oligonucleotide primers used in the PCR reaction are paired oligonucleotide primers such that there are two individual primers per pair. The individual primers of each pair define the 5' end on opposite nucleotide strands of the region to be amplified such that a suitable polymerase will copy the sequence of each strand 3' to each primer on each strand to produce amplified copies (the PCR product) of the sequence between the oligonucleotide primers. The present invention utilizes a mixture of such pairs in an appropriate buffer and such a mixture can contain 1 or more such pairs and preferably contains 2 to about 12 pairs, more preferably about 3 to about 9 pairs, most preferably about 6 pairs.

The choice of oligonucleotide primers is critical to the success of the present invention. Such oligonucleotide primers should be chosen with several factors in mind. First, the oligonucleotide primers should be of a suitable length to provide specific binding to the desired insecticidal genes. Suitable lengths preferably range from about 10 to about 30 nucleotides in length, more preferably from about 15 to about 25 nucleotides in length, and most preferably about 20 nucleotides in length. The oligonucleotide primers need not exactly pair with a region of a Bt-like gene to be an appropriate oligonucleotide primer (i.e., there need not be 100 percent homology between the primer and the Bt-like gene to which it will anneal). Preferably, the homology of the primer to a region of a Bt-like gene will be at least 80 percent, more preferably 90 percent, and most preferably essentially 100 percent.

A second characteristic of an appropriate primer is that it will correspond to a homologous region found in many insecticidal genes of a given class. For example, Bt genes are genes that code for proteins having insecticidal activity and Bt genes of a given class produce proteins whose insecticidal activity is specific to any subgroup of insects such as an order, family or genus of insects, preferably at least at the order level, e.g., *Coleoptera, Lepidoptera, Diptera, Orthoptera*. Appropriate oligonucleotide primers could correspond to regions that are preferably 80 percent, more preferably 90 percent, and most preferably essentially percent homologous to a majority of other known insecticidal genes within a given class.

Examples of paired oligonucleotide primers that correspond to homologous regions of Bt genes of the Lepidopteran class are:

a. CCG GTG CTG GAT TTG TGT TA paired with b. AAT CCC GTA TTG TAC CAG CG; and c. CCG AGA AAG TCA AAC ATG CG paired with d. TAC ATG CCC TTT CAC GTT CC.

Examples of paired oligonucleotide primers that correspond to homologous regions of Bt genes of the Dipteran class are:

e. CAA GCC GCA AAT CTT GTG GA paired with f. ATG GCT TGT TTC GCT ACA TC; and g. GGT GCT TCC TAT TCT TTG GC paired with h. TGA CCA GGT CCC TTG ATT AC.

Examples of oligonucleotide primers that correspond to homologous regions of Bt genes of the Coleopteran class are:

i. GTC CGC TGT ATA TTC AGG TG paired with j. CAC TTA ATC CTG TGA CGC CT; and k. AGG TGC CAA CTA ACC ATG TT paired with l. GAT CCT ATG CTT GGT CTA GT.

Strains that are found to have activity against insects of the Coleopteran class are tested against primers developed to specifically identify homology to the coleopteran active gene PGS 1245. These primers are derived from the sequence of the gene as described in European patent application 0 382 990. Primer NC107 corresponds to nucleotides 131 to 148 of the PGS 1245 gene. Primer NC108 corresponds to nucleotides 632 to 651. The primers produce a 520 bp PCR product. The primers are:

m. CTG AGA GGG AAC AAC CTG; paired with n. CTC AAT GTT GTT CTG AGT GA

As a positive control for the functioning of the PCR reaction, oligonucleotide primers are prepared that correspond to a non-endotoxin gene common to all strains of *Bacillus thuringiensis*. Examples of oligonucleotide primers that are useful as a positive control are:

o. CGC TAT CAA ATG GAC CAT GG, paired with p. GGA CTA TTC CAT GCT GTA CC.

The positive control primers identify a phosphatidylinositol-specific phospholipase C (PI-PLC) from *Bacillus thuringiensis*. The primers are derived from a sequence of the gene found in Genbank (accession #X14178). See Lechner et al., *Mol. Microbiol.* 3:621-626 (1989). Primers are made to nucleotides 258 to 278 and 807 to 827 where nucleotide 1 represents the first nucleotide of the start codon. The primers give a 569 bp PCR product.

Sources of sequence data for determining homologous regions can be from any other source known to those of skill in the art, including published sequence data, GeneBank, etc.

A third characteristic of an appropriate primer is that the distance between the individual oligonucleotide primers is sufficient to produce a PCR product of detectable length. Preferably, the distance between the oligonucleotide primers is at least 100 nucleotide base pairs, more preferably from about 300 to about 1200 nucleotide base pairs. Different primer pairs to be used in the same reaction can be chosen to yield amplified products of different lengths to expedite identification of the insecticidal gene.

A fourth characteristic of an appropriate primer pair is that a sufficient portion of the nucleotides occurring between the oligonucleotide primers on at least one strand of the amplified DNA will correspond to a coding region for a protein having some insecticidal activity.

An optional fifth characteristic of an appropriate primer may be that it have a suitable adenine and thymine content to assure appropriate annealing energy. The two hydrogen bonds of adenine to thymine bonding should occur in about 40 to about 60 percent of bonds formed between the primer and the insecticidal gene to which it will anneal. Most preferably, the two hydrogen bonds of adenine to thymine bonding should occur between about 50 percent of nucleotides forming bonds between the primer and the insecticidal gene to which it will anneal.

The exposure of the second mixture to an appropriate polymerase is for a time sufficient to allow production of copies of DNA sequences between the oligonucleotide primers in a detectable amount. A sufficient time is usually time sufficient to allow from about 15 to 50 cycles of the PCR steps of denaturation, primer annealing, and primer extension. A detectable amount is any amount of PCR product that can be observed by conventional techniques. Preferably, the PCR products are detected and analyzed with ethidium bromide-stained agarose gel electrophoresis, Southern blotting/probe hybridization, or fluorescence assay.

The analysis of the PCR products includes designating Bacillus strains corresponding to the appropriate prepared cell material as candidates for possessing an unidentified Bt-like gene. This analysis involves a comparison of the PCR products for a given prepared cell material sample with the PCR products that would be expected from the primer mixture used in an individual PCR reaction containing a known insecticidal gene. PCR products produce a pattern or "fingerprint" in whatever analysis technique is used, with the pattern reflecting physical properties such as nucleotide sequence length and nucleotide content. A discernible difference in PCR product pattern of the prepared cell material would indicate a change in the nucleotide sequence when compared to the nucleotide sequence from which the oligonucleotide primers are derived.

For a Bacillus strain to be designated as a potential source of an unidentified insecticidal protein gene, the PCR product pattern for its prepared cell material should be significantly different from the PCR product pattern that would be expected from the source of the oligonucleotide primers. A significant difference in PCR product pattern would be any difference that is observable and which is more than could reasonably be attributed to error or experimental variation by one of skill in the art. For example, for a PCR product pattern that is produced using ethidium bromide-stained agarose gel electrophoresis or Southern blotting/probe hybridization, a significant difference in the pattern would be a band width. For a PCR product pattern produced by a fluorescence assay, a significant difference in the pattern would be band width and color. Any absence of detectable PCR products would also be considered as a significant difference. Moreover, any difference in the pattern relating to the types of insect activity found using certain oligonucleotide primers could also be a significant difference. For example, if oligonucleotide primers for one type of insect class, e.g., Coleopteran, Lepidopteran, or Dipteran, were used in the PCR reaction, any PCR product pattern that is different than that expected for the type of insect class primer used would be a significant difference. Thus, if for example, oligonucleotide primers corresponding to homologous regions of numerous Coleopteran specific insecticidal genes were used as oligonucleotide primers, the PCR product pattern would be considered significantly different even if the PCR pattern were an essential match to a Lepidopteran specific insecticidal gene, for example. In other words, a significant difference in the toxicity profile shown by the PCR product pattern from the toxicity profile expected using a given set or group of oligonucleotide primers, would also be considered a significant difference of the PCR products for purposes of this invention.

Once a Bacillus strain has been designated as a candidate for containing an unidentified insecticidal gene, one aspect of the present invention involves further verifying that the protein produced by the unidentified insecticidal gene has insecticidal activity. First, a protein assay sample comprising the protein coded for by the unidentified insecticidal gene of a designated microorganism strain can be obtained. This protein assay sample can be obtained by methods that are known to those of skill in the art.

For example, lyophilized spore crystal preparations can be obtained. Such a preparation contains dehydrated components of one or more of the following: cells from Bt-like Bacillus candidate, toxin crystals from Bt-like Bacillus candidate, and spores from Bt-like Bacillus candidate. Another source of a protein assay sample can be obtained using the PCR product as a probe to identify and isolate the insecticidal gene from the insecticidal microorganism candidate and expression of the isolated gene in a gene expression system. Such a gene expression system can be any such system known in the art, e.g., transformed *E. coli*, transformed plants, transformed yeast, baculovirus mediated expression, etc.

The protein assay sample thus obtained can then be tested in an insect bioassay for insecticidal activity as defined above. For example, the protein assay sample can be incorporated into the feed for an insect to be tested for insecticidal activity. Preferably insects of several different types will be used in assays for insecticidal activity such that a toxicity profile can be established for any protein produced by an unidentified insecticidal gene. Preferably, the types of insects to be used in assays for insecticidal activity include Coleopterans, Lepidopterans, Dipterans and Orthopterans.

Once the insecticidal activity of the protein produced by an unidentified insecticidal gene is determined, and preferably a toxicity profile constructed, various physical properties of the protein assay sample can be obtained and compared to the physical properties of known insecticidally active Bt toxins. Preferably, the protein assay sample for which physical properties are obtained will be a relatively pure sample of the unidentified insecticidal gene protein product substantially free from other proteins and cell material. Various physical properties and the methods of determining them are known to those of skill in the art. Such physical properties include immunological crossreactivity, size, weight, length, electrical charge, spectrophotometric properties, etc.

Using the methods of the present invention, large numbers of Bacillus strains can be screened to determine those that are candidates for containing unidentified insecticidal genes that code for insecticidal proteins. Such unidentified insecticidal proteins can then be useful as insecticidal compounds in insecticidal pesticide formulations. Such insecticidal genes can also be useful to transform plants with known techniques to obtain plants that will produce the insecticidal proteins, thus providing an alternative to the use of chemical pesticides.

Insecticidal activity can be determined using standard feeding assays on target insects. Usually, the suspected insecticidal protein is mixed with the diet by combining with the feed or applying the protein to a target plant, such as by spraying.

For example, qualitative insect toxicity testing can be carried out on lyophilized spore-crystal preparations grown in T3 broth. Stock suspensions of 1 mg spore-crystal mix/ml sterile water are prepared for each isolate tested in all bioassays. An isolate is considered positive if it caused significantly higher mortality than the controls.

For example, B. thuringiensis isolates can be tested for their activity against insects in the order Lepidoptera by using the European corn borer, Ostrinia nubilalis, and the tobacco hornworm, Manduca sexta. For both species, 30 ul of a stock spore-crystal suspension is pipetted onto disks cut from artificial Black cutworm diet, preferably about 0.5 cm (Bioserv, Inc., Frenchtown, NJ; F9240). Disks are placed in petri dishes, preferably singly in 50 mm × 10 mm snap-cap petri dishes and 1 neonatal larva of either species is added to each disk. Mortality is recorded after about 4 days.

The activity of Bt isolates against a Coleopteran insect can be tested by using, for example, the Colorado potato beetle, Leptinotarsa decemlineata. The spore-crystal suspensions used in these assays preferably contain a wetting agent, such as 0.1% Triton X-100. Plant leaflets, preferably tomato, are excised from plants and dipped into stock suspensions, air dried, and placed in petri dishes. Mortality is recorded after about 3 days.

Dipteran activity of the isolates can be tested by using, for example, Culex pipiens (mosquitoes). About ten third-instar mosquitoes are added to sterile water. After an adjustment period of at least about 30 minutes, at least 10 ug, preferably 100 ug, of a spore-crystal mix is added. Mortality is recorded after about 24 hours.

Bioassays for corn rootworms can be conducted as follows. Western corn rootworm (WCRW) eggs are obtained, e.g, from French Agricultural Research, Inc., Rte. 2, Box 294, Lamberton, Minn. 56152. Eggs are placed in an incubator at about 26° C. until eggs hatch (approximately 2 weeks). Assays are initiated as soon after hatching as possible.

Strains being tested are incorporated into a suitable artificial diet. An example of a suitable diet includes:

| | |
|---|---|
| raw wheat germ | 30.3 g |
| sucrose | 42.0 g |
| vitamin-free casein | 36.0 g |
| alphacel | 16.0 g |
| Wesson salt mix | 10.0 g |
| Vanderzant vitamin mix | 10.0 g |
| methyl parabenzoic acid | 0.7 g |

| -continued | |
|---|---|
| sorbic acid | 0.4 g |
| cholesterol | 0.067 g |
| raw linseed oil | 0.44 ml |
| aureomycin | 0.070 g |
| streptomycin | 0.070 g |
| 10% KOH | 9.3 g |
| formalin | 1.2 ml |

A portion of the diet is placed on a filter pad wet with sterile $dH_2O$ in a petri dish. Fifteen to twenty neonate WCRW larvae are placed on each portion of diet. The lid is placed on the dish and sealed with parafilm. Dishes are placed in an incubator at about 26° C. Diet is changed several days later (a new dish and filter pad are used when diet is changed to help eliminate microbial contamination) and results recorded on about day 7.

Using the procedures described above and in the examples below, four strains of Bacillus thuringiensis are identified which demostrate significant toxic activity against Coleoptera. These strains are shown to be novel compared to known Bacillus thuringiensis strains, including those known to possess activity against Coleoptera.

EXAMPLES

The following examples serve to illustrate the present invention without limiting it in any way.

EXAMPLE 1

Isolation of Spore-forming Bacillus Strains from Soil or Insect Samples

About 0.5 grams of soil are subjected to acetate selection [Travers et al., Appl. Environ. Microbiol. 53:1263–1266 (1987)] as modified in the following way to increase the efficiency of isolation of cry+bacteria from field samples.

Approximately 0.5 g of field sample is added to 10 ml of L broth (per liter: 10 g of tryptone [Difco], 5 g of yeast extract [Difco], 5 g of NaCl) in a 125 ml conical flask. In the case of insect samples, the cadavers are homogenized in 1 ml of L broth, the homogenate being returned to the flask for incubation. The L broth is supplemented with sodium acetate (0.25 M, pH 6.8). A control flask that contained no sample is included in order to check for contamination during the isolation procedure. The mixture is incubated (4 hr, 200 rpm, 30° C.) and an aliquot of 1 ml is pasteurized (65° C., 10 min) in a prewarmed 5 ml glass test tube, then spread-plated (undiluted and $10^{-1}$ dilution) on half strength L agar, and incubated for 48 hr at 30° C. Anywhere from 1 to 30 different colony types are usually obtained. The cultures are then examined for the presence of parasporal crystals using phase-contrast microscopy. Crystal forming (i.e., Cry+) strains are then purified by sub-culturing on nutrient agar (Difco) until cultures are axenic as indicated by eye and microscopic examination. Non-crystal forming (i.e., Cry−) colonies with Bt morphology are re-streaked on nutrient agar and again checked for crystal production after 48 hr, since many isolates do not produce crystals until the second or third passage after acetate treatment. Subsequent passages on nutrient agar after acetate treatment frequently give a larger number and greater diversity of cry+isolates from most samples.

Crystal producing strains are grown up in 300 ml T3 medium (Travers et al., Appl. Environ. Microbiol.

53:1263–1266 (1987)) at 30° C. and 200 rpm until sporulation is complete. Sporulation is monitored by phase-contrast microscopy. The broths are then centrifuged and the pellets resuspended in distilled water (to remove exotoxin that might be present in the broth) and lyophilized. The dry powders are then bioassayed to identify biological activity.

EXAMPLE 2

Selection and Synthesis of Oligonucletide Primers for PCR Reaction

Known nucleotide sequences of *Bacillus thuringiensis* crystal protein genes represent fourteen distinct genes, which can be classified on the basis of nucleotide sequence and insecticidal activity. CryIA crystal protein genes that exhibit insecticidal activity against Lepidoptera share extensive DNA sequence homology. Similarly, CryIV genes that code for crystal protein genes with Dipteran activity share extensive regions of homology at their 3' ends [Hofte and Whiteley, Microbiol. Reviews 53:242–255 (1989)]. Coleopteran active genes are in class Cry III. Synthetic oligonucleotides (primers) are made that correspond to the regions of homology specific for three insecticidal groups; Lepidopteran, Dipteran, and Coleopteran. These group-specific oligonucleotide primers are used to amplify and identify specific DNA sequences in Bt strains using PCR (polymerase chain reaction) technology [Saiki et al., Science 239:487–491 (1988)].

Oligonucleotide primers are selected such that each insecticidal gene group is identified by a specific set of PCR products of characteristic sizes (and color when using fluorescent dye-labelled oligonucleotide primers, see below). Oligonucleotides are synthesized on an Applied Biosystems synthesizer 380A with reagents and conditions supplied by the manufacturer. The following oligonucleotide primers are synthesized:

| Primer: | Sequence: | Gene: | Nucleotides |
|---|---|---|---|
| Lep1A: | (5')CCGGTGCTGGATTTGTGTTA(3'): | B.t. $k^1$: | 310–330 |
| Lep1B: | (5')AATCCCGTATTGTACCAGCG(3'): | B.t. $k^1$: | 780–800 |
| Lep2A: | (5')CCGAGAAAGTCAAACATGCG(3'): | B.t. $k^1$: | 2158–2178 |
| Lep2B: | (5')TACATGCCCTTTCACGTTCC(3'): | B.t. $k^1$: | 3046–3066 |
| Dip1A: | (5')CAAGCCGCAAATCTTGTGGA(3'): | B.t. $i^2$: | 2551–2571 |
| Dip1B: | (5')ATGGCTTGTTTCGCTACATC(3'): | B.t. $i^2$: | 3328–3348 |
| Dip2A: | (5')GGTGCTTCCTATTCTTTGGC(3'): | B.t. $i^2$: | 740–760 |
| Dip2B: | (5')TCACCAGGTCCCTTGATTAC(3'): | B.t. $i^2$: | 2010–2020 |
| Col1A: | (5')GTCCGCTGTATATTCAGGTG(3'): | B.t. $t^3$: | 1801–1821 |
| Col1B: | (5')CACTTAATCCTGTGACGCCT(3'): | B.t. $t^3$: | 2430–2450 |
| Col2A: | (5')AGGTGCCAACTAACCATGTT(3'): | B.t. $t^3$: | 621–641 |
| Col2B: | (5')GATCCTATGCTTGGTCTAGT(3'): | B.t. $t^3$: | 1661–1681 |

The references are:
[1]B.t. *kurstaki cryα*, Geiser et al., Gene 48:109–118 (1986)
[2]B.t. *israelensis* HD567, Yamamoto et al., Gene 66:107–120 (1988)
[3]B.t. *tenebrionis*, Hoefte et al., Nucleic Acids Res. 15:7183–7783 (1987)

Two sets of oligonucleotide primers specific for each of the three insecticidal groups are included in each PCR reaction. Lepidopteran-specific oligonucleotide primers Lep1A and Lep1B give a 489 bp PCR product with cryIA(a), cryIA(b), and cryIA(c) crystal genes. Oligonucleotide primers Lep2A and Lep2B give two different size products depending on the type of cryIA gene. CryIA(a) and cryIA(c) genes are identified by a 986 bp PCR product and cryIA(b) by a 907 bp product. Dipteran-specific oligonucleotide primers Dip1A, Dip1B, and Dip2A, Dip2B give 796 bp and 1290 bp products, respectively with the israelensis cryIV genes. CryIVA genes are identified by both the 796 bp and 1290 products, whereas the cryIVB genes only give the 796 bp product. Coleopteran-specific oligonucleotide primers Col1A, Col1B and Col2A, Col2B give a 650 bp and a 1060 bp product respectively with the *B. thuringiensis tenebrionisis* cryIIIA gene. The Coleopteran-active *B. thuringiensis tolworthi* cryIIIB gene is also identified by a 1060 bp product, but does not give a 650 bp product.

EXAMPLE 3

Sample Preparation for PCR Reaction

A loopful of cells from a *Bacillus thuringiensis* colony from an overnight nutrient agar plate is transferred to a 0.5 ml GeneAmp Reaction tube (Perkin Elmer Cetus) containing 50 ul PCR reaction mix. The PCR reaction mix is as described in the GeneAmp Kit (Perkin Elmer Cetus) with the addition of 0.1–0.5 uM of each of the twelve Bt oligonucleotide primers and minus the Taq polymerase. The microcentrifuge tube is transferred to a boiling waterbath for ten minutes to lyse the cells. AmpliTaq polymerase (Perkin Elmer Cetus), 0.1–1.0 ul is added to each tube, mixed, and overlaid with a few drops of mineral oil.

EXAMPLE 4

Reaction Conditions for PCR

PCR is performed in a 50 ul reaction volume using reagents from GeneAmp kit (Perkin Elmer Cetus). Amplification is accomplished using the DNA Thermal Cycler (Perkin Elmer Cetus Instruments) using the "Step-Cycle" program set to denature at 94° C. for 45 seconds, anneal at 45° C. for 45 seconds, extend at 72° C. for one minute including a 4 second extension for each for a total of 35 cycles.

EXAMPLE 5

PCR Product Analysis on Agarose Gels

Following amplification, 20 ul of the PCR reaction mix is loaded on a 0.8% agarose TBE (TRIS-borate) gel, stained with ethidium bromide and photographed.

EXAMPLE 6

Conjugation of Fluorescent Dyes to PCR Primers

PCR primers Lep1A, Lep1B and Col1A, Col1B are synthesized with a 5' primary amino group (aminolink-2, Applied Biosystems) on an Applied Biosystems DNA Synthesizer. Applied Biosystems fluorescent NHS ester dyes, 5'-carboxyfluorescein (FAM) and 6-carboxy-X-rhodamine (ROX) are conjugated to the oligonucleotides [Chehab and Kan, Proc. Nat. Acad. Sci USA 86:9178–9182 (1989)]. FAM and ROX are conjugated to the Lep and Col primers, respectively, to give green and red colored PCR products. Dye-labeled oligonucleotides are purified by Sephadex (G-25) gel-filtration followed by HPLC purification on an Aquapore 300C-8 column [Chehab and Kan, Proc. Nat. Acad. Sci USA 86:9178-9182 (1989)]. The labeled primers are used in the PCR reactions as described above. Fluorescent colored products are visualized on a long wavelength UV transilluminator.

EXAMPLE 7

Novel *Bacillus thuringiensis* Strains with Activity Against Colorado Potato Beetle.

Using the procedures described above, the following strains of *Bacillus thuringiensis* are isolated which are shown to demonstrate activity against members of the insect order Coleoptera, particularly against Colorado Potato Beetle. All four strains test positively in reaction with the positive control olgionucleotide primers, confirming their identity as members of the species *Bacillus thuringiensis*. In PCR analysis using the oligonucleotide primers described in Example 2, none of the four strains produce PCR products.

The four novel strains have been deposited with the American Type Culture Collection, in Rockville Maryland, pursuant to the Budapest Treaty.

A. Characteristics of Strain CGB 14-4, (deposited with American Type Culture Collection on Apr. 24, 1991 and accorded ATC accession number 55172.

Strain CGB 14-4 produces flat, diamond shaped crystals. PCR analysis using the primers described in Example 2 above shows that the strain contains a gene different from that of known coleopteran active strains. No PCR product is seen. A protein of approximately 28 kilodalton in molecular weight is seen on SDS-PAGE after solubilization of crystals in pH 12 carbonate buffer. The strain demonstrates no reactivity with *Bacillus thuringiensis kurstaki* or *Bacillus thuringiensis tenebrionis* specific antibody on western blots. The strain exhibits equal or better activity when compared to *Bacillus thuringiensis tenebrionis* in Colorado Potato beetle (CPB) bioassays, as shown in Example 10 below.

B. Characteristics of Strain CGB 14-5, (deposited with American Type Culture Collection on Apr. 24, 1991 and accorded ATCC accession number 55173.

Strain CGB 14-5 produces amorphous inclusions. PCR analysis using the primers described in Example 2 above shows that strain CGB 14-5 contains a gene different from that of known coleopteran active strains. No PCR product is seen. A protein of approximately 42 kilodaltons in molecular weight is seen on SDS-PAGE after solubilization of crystals in pH 12

The strain demonstrates no reactivity with *Bacillus thuringiensis kurstaki* or *Bacillus thuringiensis tenebrionis* specific antibody on western blots. The strain exhibits equal or better activity when compared to *Bacillus thuringiensis tenebrionis* in Colorado Potato beetle (CPB) bioassays, as shown in Example 10 below.

C. Characteristics of Strain CGB 14-8, (deposited with American Type Culture Collection on Apr. 24, 1991 and accorded ATCC accession number 55176.

Strain CGB 14-8 produces flat squares and bipyramidal crystals. PCR analysis using the primers described in Example 2 above shows that strain CGB 14-8 contains a gene different from that of known coleopteran active strains. No PCR product is seen. A protein of approximately 28 kilodaltons in molecular weight is seen on SDS-PAGE after solubilization of crystals in pH 12 carbonate buffer. The strain demonstrates no reactivity with *Bacillus thuringiensis kurstaki* or *Bacillus thuringiensis tenebrionis* specific antibody on western blots. The strain exhibits equal or better activity when compared to *Bacillus thuringiensis tenebrionis* in Colorado Potato beetle (CPB) bioassays, as shown in Example 10 below.

D. Characteristics of Strain CGB 14-10, (deposited with American Type Culture Collection on Apr. 24, 1991 and accorded ATCC accession number 55177).

Strain CGB 14-10 produces small bipryamidial crystals. PCR analysis using the primer oligonucleotides described in Example 2 above show that strain CGB 14-10 contains a gene different from that of any known *Bacillus thuringiensis tenebrionis* gene. A protein of approximately 110 kilodaltons in molecular weight is seen on SDS-PAGE after solubilization of crystals in pH 12 carbonate buffer. The strain demonstrates no reactivity with *Bacillus thuringiensis kurstaki* specific antibody, but reacts with *Bacillus thuringiensis tenebrionis* specific antibody on western blots.

Strain CGB 14-10 is found to produce similar PCR products compared to strain Bt PGS 1245 when analyzed with the oligonucleotide primers described earlier which correspond to the Bt PGS 1245 strain described in European Patent Application Publication No. 0 382 990 (1990). This similarity of PCR product profiles does not necessarily indicate that the strains are closely related, nor does it necessarily indicate that the toxin genes are homologous over a substantial portion of their respective coding regions.

In order to assess the possible relationship between strain CGB 14-10 and the PGS 1245 strain, a comparison of the biochemical assay for acid production from different sugars by the Bt PGS 1245 strain and CGB 14-10 demonstrate that the two strains are substantially different. The results of the biochemical assay are shown in Table 1.

Strain CGB 14-10 exhibits equal or better activity when compared to *Bacillus thuringiensis tenebrionis* in Colorado Potato beetle (CPB) bioassays, as shown in Example 10 below.

EXAMPLE 8

Biochemical Assay of Coleopteran Active Strains

Acid production from different sugars by the strains of the present invention are determined using the API 20E and API CHB50 biochemical tests and compared with that reported for PGS 1245 using API-50CHB test strips (API Systems SA). The results are shown in Table 1, below.

TABLE 1

| Substrate: | Acid production by the CPB active strains | | | | |
|---|---|---|---|---|---|
| | 14-4 | 14-5 | 14-8 | 14-10 | PGS1245 |
| Control | − | − | − | − | − |
| Glycerol | − | − | − | + | w |
| Erythritol | − | − | − | − | − |
| D-Arabinose | − | − | − | − | − |
| L-Arabinose | − | − | − | − | − |
| Ribose | − | + | w | + | + |
| D-Xylose | − | − | − | − | − |
| L-Xylose | − | − | − | − | − |
| Adonitol | − | − | − | − | − |
| B-Methylxyloside | − | − | − | − | − |
| Galactose | − | − | − | − | − |
| D-Glucose | + | + | + | + | + |
| D-Fructose | + | + | + | + | + |
| D-Mannose | − | − | − | + | + |
| L-Sorbose | − | − | − | − | − |

TABLE 1-continued

| Substrate: | Acid production by the CPB active strains | | | | |
|---|---|---|---|---|---|
| | 14-4 | 14-5 | 14-8 | 14-10 | PGS1245 |
| Rhamnose | − | − | − | − | − |
| Dulcitol | − | − | − | − | − |
| Inositol | − | − | − | − | − |
| Mannitol | − | − | − | − | − |
| Sorbitol | − | − | − | − | − |
| a-Methyl D-mannoside | − | − | − | − | − |
| a-Methyl D-glucoside | − | − | − | − | − |
| N-Acetylglucosamine | + | + | w | + | + |
| Amygdalin | − | − | − | − | − |
| Arbutin | − | w | w | + | + |
| Esculin | − | + | − | + | + |
| Salicin | − | − | − | + | w |
| Cellobiose | − | − | − | + | − |
| Maltose | + | + | + | + | + |
| Lactose | − | − | − | − | − |
| Melibiose | − | − | − | − | − |
| Saccharose | − | + | − | + | + |
| Trehalose | + | + | + | + | + |
| Inuline | − | − | − | − | − |
| Melezitose | − | − | − | − | − |
| D-Raffinose | − | − | − | − | − |
| Starch | + | + | + | + | + |
| Glycogen | + | + | + | + | + |
| Xylitol | − | − | − | − | − |
| B-Gentiobiose | − | − | − | − | − |
| D-Turanose | − | − | − | − | − |
| D-Lxyose | − | − | − | − | − |
| D-Tagatose | − | − | − | − | − |
| D-Fucose | − | − | − | − | − |
| D-Arabitol | − | − | − | − | − |
| Gluconate | − | − | − | w | − |
| 2-Ketogluconate | − | − | − | − | − |
| 5-Ketogluconate | − | − | − | − | − |
| Arginine dihydrolase | + | + | + | − | + |
| Gelatin | + | + | + | + | + |
| Nitrate Reduction | − | − | − | − | + |

+ = positive reaction
− = negative reaction
w = weakly positive reaction
All tests used the API 20E and API CHB50 biochemical tests and were done as described by API System Inc.

EXAMPLE 9

Bioassay of Isolated Strains and Correlation with PCR Product Profile

Qualitative insect toxicity testing is carried out on lyophilized spore-crystal preparations grown in T3 broth. Stock suspensions of 1 mg spore-crystal mix/ml sterile water are prepared for each isolate tested in all bioassays. An isolate is considered positive if it causes significantly higher mortality than the controls.

B. thuringiensis isolates are tested for their activity against insects in the order Lepidoptera by using the European corn borer, *Ostrinia nubilalis*, and the tobacco hornworm, *Manduca sexta*. For both species, 30 ul of a stock spore-crystal suspension is pipetted onto 0.5 cm disks cut from artificial Black cutworm diet (Bioserv, Inc., Frenchtown, N.J.). Disks are placed singly in 50 mm × 10 mm snap-cap petri dishes and 1 neonatal larva of either species is added to each disk. Twenty larvae of both species are tested for each Bt isolate. Mortality is recorded after 4 days.

The activity of Bt isolates against a Coleopteran insect is tested by using the Colorado potato beetle, *Leptinotarsa decimlineata*. The spore-crystal suspensions used in these assays contained 0.1% Triton X-100 as a wetting agent. Tomato leaflets are excised from 30 cm plants and dipped into stock suspensions, air dried, and placed in 50 mm × 10mm petri dishes. Three replicates of 5 first-instar larvae are tested for each Bt isolate. Mortality is recorded after 3 days.

Dipteran activity of the isolates is tested by using *Culex pipiens* mosquitoes. Ten third-instar mosquitoes are added to 10 ml of sterile water in 30 ml plastic cups. After a 30 minute adjustment period, 100 ug of a spore-crystal mix is added. Mortality is recorded after 24 hours.

Bioasays for corn rootworms is conducted as follows. Western corn rootworm eggs are obtained from French Agricultural Research, Inc., Rte. 2, Box 294, Lamberton, Minn. 56152. Non-diapausing WCRW eggs arrive in 100 × 15 mm petri dish between two pieces of moistened filter paper. The dish is well sealed with parafilm. Upon arival, the dish is placed in a 26° C. incubator until eggs hatch (aprox. 2 weeks). Assays are set up as soon after hatching as possible.

Strains being tested are incorporated into artificial diet consisting of:

| raw wheat germ | 30.3 g |
|---|---|
| sucrose | 42.0 g |
| vitamin-free casein | 36.0 g |
| alphacel | 16.0 g |
| Wesson salt mix | 10.0 g |
| Vanderzant vitamin mix | 10.0 g |
| methyl parabenzoic acid | 0.7 g |
| sorbic acid | 0.4 g |
| cholesterol | 0.067 g |
| raw linseed oil | 0.44 ml |
| aureomycin | 0.070 g |
| streptomycin | 0.070 g |
| 10% KOH | 9.3 g |
| formalin | 1.2 ml |

One quarter of the diet is placed on a filter pad (Fischer #08-757-20BO wet with 5600 ul of sterile dH$_2$O in a 50 × 9 mm dish (Fischer #08-757-19). Fifteen to twenty neonate WCRW larvae are placed on each piece of diet. The lid is placed on the dish and sealed with parafilm. Dishes are placed in a 26° C. incubator. Diet is changed on day 4 (a new dish and filter pad are used when diet is changed to help eliminate contamination) and results recorded on day 7.

Known *Bacillus thuringiensis* strains obtained from the USDA, as well as strains isolated from soil samples are analyzed by PCR. Each PCR reaction contains twelve Bt primers to amplify products characteristic for each of the three insecticidal groups. PCR analysis of over thirty known Bt strains using the twelve Bt PCR primers gives characteristic PCR products corresponding to the insecticidal activity of each strain. Strains with no known insecticidal activity do not give any PCR products. Thirty-two USDA strains analyzed by PCR and the presence of characteristic products are shown in Table 2.

Spore-forming strains isolated from soils are analyzed by PCR and insecticidal activity predicted on the basis of PCR product profile. PCR analysis of over twenty-five soil isolates gives characteristic products that allow rapid prediction of insecticidal activity. Isolates are tested in bioassays against European corn borer, Colorado potato beetle, and mosquito Culex larvae to confirm insecticidal predictions. Table 3 shows the PCR results of representative soil and insect cadaver isolates and correlation to insect bioassays. As shown in Table 3, the PCR screen has 100% correlation to insect bioassays.

TABLE 2

PCR ANALYSIS OF KNOWN BT STRAINS

| BT STRAIN | | PCR PRODUCT | INSECTICIDAL ACTIVITY |
|---|---|---|---|
| HD-1 | kurstaki | Lep: 489 bp, 907 bp, 986 bp | Lep |
| HD-73 | kurstaki | Lep: 489 bp, 986 bp | Lep |
| B-4039 | berliner | Lep: 489 bp, 907 bp | Lep |
| B-4042 | sotto | Lep: 489 bp, 907 bp, 986 bp | Lep |
| B-4044 | kenyae | Lep: 489 bp, 986 bp | Lep |
| B-4049 | morrisoni | Lep: 489 bp, 986 bp | Lep |
| B-4057 | subtoxicus | Lep: 489 bp, 907 bp | Lep |
| B-4060 | thompsoni | Lep: 986 bp | Lep |
| HD-501 | ostriniae | Lep: 489 bp, 907 bp | Lep |
| HD-22 | thuringiensis | Lep: 489 bp, 986 bp | Lep |
| HD-9 | entomocidus | Lep: 489 bp, 986 bp | Lep |
| HD-11 | aizawai | Lep: 489 bp, 986 bp | Lep |
| HD-68 | aizawai | Lep: 489 bp, 986 bp | Lep |
| HD-110 | entomocidus | Lep: 489 bp, 986 bp | Lep |
| HD-198 | entomocidus | Lep: 489 bp, 907 bp, 986 bp | Lep |
| HD-131 | aizawai | Lep: 489 bp, 907 bp, 986 bp | Lep |
| HD-133 | aizawai | Lep: 489 bp, 907 bp, 986 bp | Lep |
| HD-64 | kenyae | Lep: 489 bp, 907 bp | Lep |
| HD-37 | dendrolimus | Lep: 489 bp, 986 bp | Lep |
| HD-14 | thuringiensis | Lep: 489 bp, 986 bp | Lep |
| HD-567 | israelensis | Dip: 796 bp, 1290 bp | Dip |
| B-4554 | israelensis | Dip: 796 bp, 1290 bp | Dip |
| HD-489 | pakistani | no PCR products | none known |
| HD-521 | indiana | no PCR products | none known |
| HD-511 | dakota | no PCR products | none known |
| HD-866 | tohokuensis | no PCR products | none known |
| HD-868 | tochigiensis | no PCR products | none known |
| HD-867 | kumamotoensis | no PCR products | none known |
| BI-256-82 | tenebrionis | 650 bp, 1060 bp | Col |

TABLE 3

PCR ANALYSIS OF PREVIOUSLY UNIDENTIFIED BT STRAINS

| Strain No. | PCR Products | Antibody Reactivity | Insect Activity | Protein Pattern |
|---|---|---|---|---|
| 1-9-2 | BTT | NT | CPB | 68 Kd, 60 Kd |
| 3-5 | HD1 | NR | THW | 130 Kd, 67 Kd |
| 13-3 | BTT | BTT | CPB | 68 Kd, 60 Kd |
| 14-4 | NI | NR | CPB | 28 Kd |
| 14-5 | NI | NR | CPB | 42 Kd |
| 14-8 | NI | NR | CPB | 28 Kd |
| 14-10 | NI* | BTT | CPB | 110 Kd |

NI = None identified
BTT = *Bacillus thuringiensis* variety *tenebrionis*
HD1 = *Bacillus thuringiensis* variety *kurstaki*
NI* = Product from primers for the endotoxin gene of strain PGS 1245, as described in EP 0 382 990 A1.
NR = No reactivity identified
NT = Not tested
CPB = Colorado Potato Beetle (*Coleoptera*)
THW = Tobacco Horn Worm (*Lepidoptera*)

EXAMPLE 10

TOXICITY TO COLORADO POTATO BEETLE COMPARED TO *BACILLUS THURINGIENSIS* VAR. TENEBRIONIS

Toxin from the strains of the present invention are precipitated for toxicity determination (LC50). LC50 refers to a concentration that kills 50% of the larvae.

The assay for the Colorado potato beetle is conducted as follows:

Known weights of acetone precipitated Bt powders are suspended in 0.1% Triton X-100 to give a final concentration of 1000 ppm. Five serial dilutions are then made from this stock suspension. Each of the five concentrations for each Bt isolate are tested by dipping four tomato leaflets, from 30 cm Rutgers tomato plants, in each concentration and allowing them to air dry. Five first instar Colorado potato beetle larvae are then placed on each leaflet giving 20 insects tested at each concentration. Mortality is recorded after 4 days. LC50' plus 95% confidence intervals (expressed in ppm) are calculated using a probit analysis method (Finney 1971) for the Apple IIE computer. The amount of insecticidal protein (ICP) in the original acetone precipitated powders is determined. The percentages of ICPs in each powder are then used to convert the LC50' from ppm to ng of ICP per ml Triton X-100. Table 4 shows the results of the assay for the four novel strains compared to *Bacillus thuringiensis* var. tenebrionis.

For example: The LC50 of Bt strain CGB 14-10 is 6 ppm. The ICP concentration of the acetone powder is 0.177%. Therefore the LC50 based on ICP content is $6 \times 0.177\% = 0.010$ ug/ml or 10 ng/ml.

TABLE 4

| BT Isolate | LC50 PPM[a] | LC50 ng ICP/ml[b] |
|---|---|---|
| 14-4 | 20 | 6 |
| 14-5 | 17 | 3 |
| 14-8 | NT | NT[c] |
| 14-10 | 6 | 10 |
| Btt | 6 | 27 |

NT = Not tested
[a] Concentration of acetone precipitated powder.
[b] Based on estimate of insecticidal protein (ICP) concentration in acetone precipitated powders.
[c] 152 ppm (116 ng ICP/ml) resulted in 100% mortality.

---

What is claimed is:

1. An isolated strain of *Bacillus thuringiensis* active against Coleopteran insects, wherein the strain of *Bacillus thuringiensis* is selected from the group consisting of CGB 14-4, CGB 14-5, CGB 14-8 and CGB 14-10.

2. An isolated strain of *Bacillus thuringiensis* according to claim 1, wherein the strain is CGB 14-4.

3. An isolated strain of *Bacillus thuringiensis* according to claim 1, wherein the strain is CGB 14-5.

4. An isolated strain of *Bacillus thuringiensis* according to claim 1, wherein the strain is CGB 14-8.

5. An isolated strain of *Bacillus thuringiensis* according to claim 1, wherein the strain is CGB 14-10.

6. A method of controlling insect pests belonging to the order of Coleoptera which comprises contacting said insect pests with an insect-controlling effective amount of a *Bacillus thuringiensis* strain selected from the group consisting of CGB 14-4, CGB 14-5, CGB 14-8 and CGB 14-10.

* * * * *